Nov. 19, 1963 H. B. LEWIS ETAL Plant Pat. 2,308
AZALEA PLANT
Filed Sept. 28, 1962 2 Sheets-Sheet 1
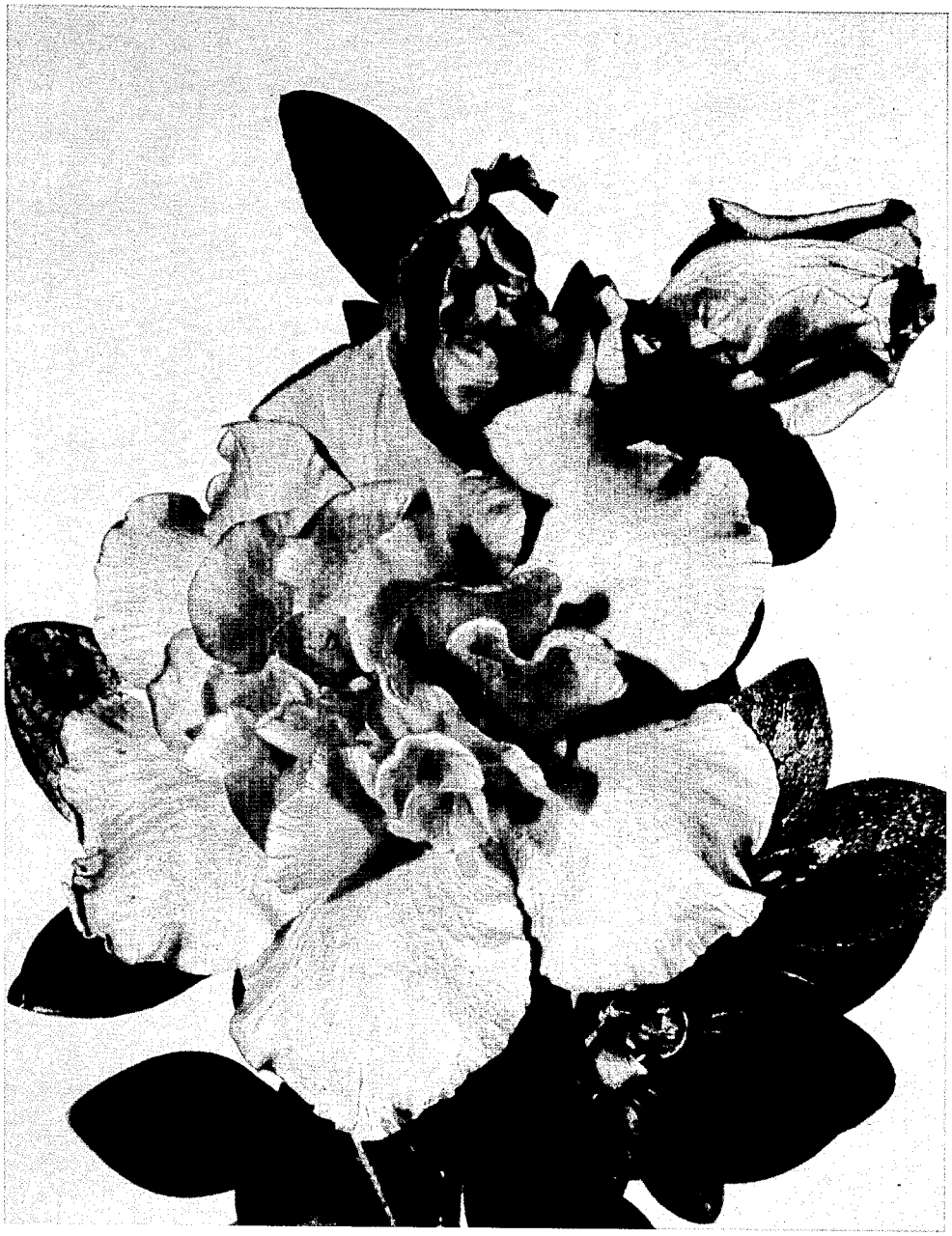
Inventors.
H. B. Lewis and
H. H. Lewis
By: Robb & Robb
Attorneys.

Nov. 19, 1963 H. B. LEWIS ETAL Plant Pat. 2,308
AZALEA PLANT
Filed Sept. 28, 1962 2 Sheets-Sheet 2
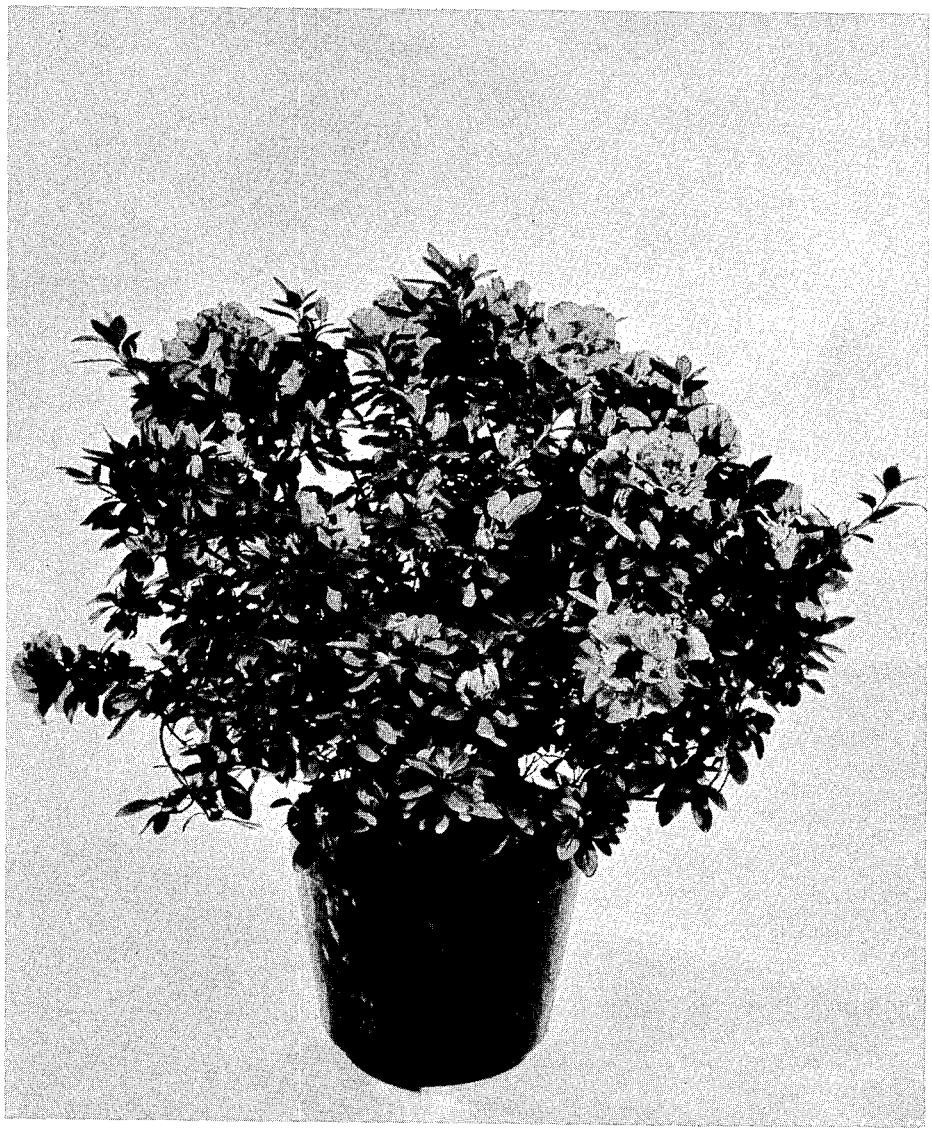
Inventors.
H. B. Lewis and
H. H. Lewis
By: Robb & Robb
Attorneys.

United States Patent Office

Plant Pat. 2,308
Patented Nov. 19, 1963

2,308
AZALEA PLANT

Hubert B. Lewis and Helen H. Lewis, both of 16562 E. Leffingwell Road, Whittier, Calif.

Filed Sept. 28, 1962, Ser. No. 227,096
1 Claim. (Cl. Plt.—57)

The present invention relates to a new and distinct variety of azalea plant which was originated by us by crossing the Belgian Indian variety known as "Chimes" (unpatented) with the Belgian Indian variety known as "Triumph" (unpatented), the former being the seed parent, and the latter being the pollen parent.

As the result of this breeding, we have produced a new azalea variety which is endowed with a new and improved combination of characteristics, as evidenced by the following features which are outstanding therein and which distinguish the new variety from its parents, as well as from all other varieties of which we are aware;

(1) A strong and vigorous habit of growth;

(2) Abundant flower production;

(3) A long blooming season which is much longer than that of either parent variety;

(4) A large flower size;

(5) An unusual combination of flower forms borne at the same time, said forms including single flowers, hose in hose, double and double hose in hose; and (6) A distinctive and attractive Spiraea Red general color tonality of the flowers.

In comparison with its pollen parent, "Triumph," our new variety somewhat resembles this parent in habit of growth and foliage, but the foliage of the new variety is better, and the flowers are larger and brighter red in color. There is no resemblance of the new variety to its seed parent, "Chimes," except that they both bear red colored flowers.

Asexual reproduction of our new variety by cuttings, as performed at Rivera, California, and at Whittier, California, shows that the foregoing characteristics and distinctions come true to form and are established and transmitted through succeeding propagations.

The accompanying drawings show a typical specimen plant of our new azalea variety as depicted in black and white to illustrate its general form and habit of growth, as well as typical specimens of the flowers and foliage as depicted in color on a somewhat enlarged scale to better illustrate the details thereof.

The following is a detailed description of our new azalea variety, with color terminology in accordance with the Wilson Horticultural Color Chart, except where general color terms of ordinary dictionary significance are obvious:

Locality where grown and observed: Whittier, California.
Propagation: Holds its distinguishing characteristics through succeeding propagations by cuttings.

*Plant*

Form: Much-branched.
Habit: Vigorous; strong; rather loose without pruning.
Rooting habit: Good; easy.

Foliage:
*Size.*—Medium.
*Quantity.*—Normal.
*Color.*—New foliage: upper side—Scheeles Green, Plate 860; under side—Spinach Green, Plate 0960/3. Old foliage: upper side—Parsley Green, Plate 00962; under side—Spinach Green, Plate 0960/3.
*Shape.*—Oval pointed.
*Texture.*—Upper side—slightly corrugated by veins. Under side—rough, due to veins.
*Margin.*—Smooth.
*Aspect.*—Good.
*Disease resistance.*—Relatively free from ordinary diseases to which azalea plants are normally subject, as determined by comparison with other varieties grown under the same cultural conditions at Whittier, California.

*Flowers*

Borne: 2 or 3 to stem; on fairly short stems.
Blooming habit: Blooms freely and evenly.
Blooming season: Normally in spring, but very suitable for forcing.
Quantity of bloom: Free, both outdoors and in greenhouse.
Continuity: One season heavy and then intermittent, as grown in California.
Petalage: Normally 5 outer petals, with raised tufted center, but frequently there is a great variation of flower form on same plant, ranging from single flowers with 5 petals to very double flowers with 10 petals and very double center, said range covering single flowers, hose in hose, double and double hose in hose.
*Color.*—Spiraea Red, Plate 025.
*Texture.*—Medium.
*Appearance.*—Inside—raised double center. Outside—slightly ruffled, with outer petals slightly incurved at times.
*Shape.*—Ovate; oblong.
*Arrangement.*—Belgian Indian type double flower.
Bud: Color—Spiraea Red, Plate 025.

*Reproductive Organs*

Stamens: Scarce. Color—Spiraea Red.
Pollen: Sparse. Color—white.
Styles: Color—Spiraea Red.
Ovaries: Normal.

We claim:

A new and distinct variety of azalea plant, substantially as herein shown and described, characterized particularly as to novelty by the unique combination of a strong and vigorous habit of growth, abundant flower production, a long blooming season, large flower size, an unusual combination of flower forms borne at the same time, including single flowers, hose in hose, double, and double hose in hose flowers, and a distinctive and attractive Spiraea Red general color tonality of the flowers.

No references cited.